(12) United States Patent
Nelson

(10) Patent No.: US 9,539,382 B2
(45) Date of Patent: Jan. 10, 2017

(54) STEPPED CATHETERS WITH FLOW RESTRICTORS AND INFUSION SYSTEMS USING THE SAME

(71) Applicant: Medtronic, Inc., Minneapolis, MN (US)

(72) Inventor: Brian D. Nelson, Birchwood, MN (US)

(73) Assignee: Medtronic, Inc., Minneapolis, MN (US)

( * ) Notice: Subject to any disclaimer, the term of this patent is extended or adjusted under 35 U.S.C. 154(b) by 761 days.

(21) Appl. No.: 13/795,539

(22) Filed: Mar. 12, 2013

(65) Prior Publication Data

US 2014/0276417 A1    Sep. 18, 2014

(51) Int. Cl.
*A61M 5/14* (2006.01)
*A61M 25/00* (2006.01)
*A61M 5/142* (2006.01)

(52) U.S. Cl.
CPC ......... *A61M 5/141* (2013.01); *A61M 5/14276* (2013.01); *A61M 25/0023* (2013.01); *A61M 25/0084* (2013.01); *A61M 25/007* (2013.01); *A61M 2005/1406* (2013.01); *A61M 2025/0042* (2013.01); *A61M 2025/0089* (2013.01); *A61M 2210/0693* (2013.01)

(58) Field of Classification Search
CPC .................. A61M 25/007; A61M 2039/0223; A61M 2210/0693; A61M 39/0208; A61M 5/141; A61M 31/002; A61M 2025/0091; A61M 2005/1406; A61M 2025/0089; A61M 25/0068; A61M 25/003; A61M 5/3145; A61M 2005/1652; A61M 2005/1655; A61M 2005/1657; A61M 2039/0241; A61M 25/0084; A61M 2025/0042; A61M 25/0023; A61M 5/14276
See application file for complete search history.

(56) References Cited

U.S. PATENT DOCUMENTS

| | | | |
|---|---|---|---|
| 3,626,959 | A | 12/1971 | Santomieri |
| 3,671,979 | A | 6/1972 | Moulopoulos |
| 3,951,147 | A | 4/1976 | Tucker et al. |
| 4,176,683 | A | 12/1979 | Leibinsohn |

(Continued)

FOREIGN PATENT DOCUMENTS

| | | |
|---|---|---|
| EP | 0 287 247 A2 | 10/1988 |
| EP | 0 287 247 A3 | 8/1989 |

(Continued)

OTHER PUBLICATIONS

"Flexible Fused Silica Capillary Tubing," Polymicro Technologies, Phoenix, AZ, © 2011; 1 page.

(Continued)

*Primary Examiner* — Bhisma Mehta
*Assistant Examiner* — Brandy S Lee
(74) *Attorney, Agent, or Firm* — Mueting, Raasch & Gebhardt, P.A.

(57) ABSTRACT

A stepped catheter comprising a distal portion of smaller diameter than a proximal portion, wherein the distal portion defines a flow aperture configured to deliver fluid passing through the catheter from the proximal portion to the flow aperture. The catheter may include a flow restrictor located within a lumen of the catheter at or near the flow aperture. A filter element may also be included and located within the lumen of the catheter at a location upstream of the flow restrictor.

22 Claims, 3 Drawing Sheets

(56) References Cited

U.S. PATENT DOCUMENTS

| | | | |
|---|---|---|---|
| 4,397,335 A | 8/1983 | Doblar et al. | |
| 4,411,292 A | 10/1983 | Schiller | |
| 4,550,748 A | 11/1985 | Nunez | |
| 4,717,379 A * | 1/1988 | Ekholmer | A61M 25/007 604/43 |
| 4,759,752 A | 7/1988 | Stöber | |
| 4,798,226 A | 1/1989 | Struth | |
| 4,834,704 A | 5/1989 | Reinicke | |
| 5,006,997 A | 4/1991 | Reich | |
| 5,279,544 A | 1/1994 | Gross et al. | |
| 5,294,325 A * | 3/1994 | Liu | 204/418 |
| 5,342,298 A | 8/1994 | Michaels et al. | |
| 5,395,352 A | 3/1995 | Penny | |
| 5,531,684 A | 7/1996 | Ensminger et al. | |
| 5,558,640 A | 9/1996 | Pfeiler et al. | |
| 5,605,545 A | 2/1997 | Nowosielski et al. | |
| 5,746,722 A | 5/1998 | Pohndorf et al. | |
| 5,820,589 A | 10/1998 | Torgerson et al. | |
| 5,893,838 A | 4/1999 | Daoud et al. | |
| 5,899,873 A | 5/1999 | Jones et al. | |
| 5,928,195 A | 7/1999 | Malamud et al. | |
| 5,999,857 A | 12/1999 | Weijand et al. | |
| 6,179,806 B1 | 1/2001 | Sansoucy | |
| 6,203,523 B1 | 3/2001 | Haller et al. | |
| 6,551,290 B1 | 4/2003 | Elsberry et al. | |
| 6,569,128 B1 * | 5/2003 | Christensen et al. | 604/246 |
| 6,585,681 B2 | 7/2003 | Brugger et al. | |
| 6,689,085 B1 | 2/2004 | Rubenstein et al. | |
| 6,749,581 B2 | 6/2004 | Thompson et al. | |
| 6,893,429 B2 | 5/2005 | Petersen | |
| 6,945,969 B1 | 9/2005 | Morris et al. | |
| 7,217,251 B2 | 5/2007 | Olsen et al. | |
| 7,513,884 B2 | 4/2009 | Miesel et al. | |
| 7,763,007 B2 | 7/2010 | Miesel et al. | |
| 7,766,860 B2 | 8/2010 | Olsen et al. | |
| 2002/0087147 A1 * | 7/2002 | Hooper | A61M 5/141 604/892.1 |
| 2002/0107471 A1 | 8/2002 | Thompson et al. | |
| 2004/0199128 A1 | 10/2004 | Morris et al. | |
| 2005/0075624 A1 | 4/2005 | Miesel | |
| 2005/0090799 A1 | 4/2005 | Morris | |
| 2005/0241387 A1 | 11/2005 | Miesel et al. | |
| 2005/0245858 A1 | 11/2005 | Miesel et al. | |
| 2005/0245867 A1 | 11/2005 | Olsen et al. | |
| 2005/0245887 A1 * | 11/2005 | Olsen | A61M 25/00 604/284 |
| 2006/0075973 A1 * | 4/2006 | Wolfe et al. | 119/6.8 |
| 2007/0043335 A1 | 2/2007 | Olsen et al. | |
| 2009/0143764 A1 | 6/2009 | Nelson | |
| 2009/0187149 A1 | 7/2009 | Nelson | |
| 2010/0217196 A1 * | 8/2010 | Nelson | 604/174 |
| 2012/0083742 A1 | 4/2012 | Nelson | |

FOREIGN PATENT DOCUMENTS

| | | |
|---|---|---|
| EP | 0 361 662 A1 | 4/1990 |
| EP | 0 287 247 B1 | 8/1992 |
| EP | 0 361 662 B1 | 6/1993 |
| EP | 0 564 321 A2 | 10/1993 |
| EP | 0 564 321 A3 | 1/1994 |
| EP | 0 564 321 B1 | 12/1996 |
| EP | 0 873 762 A2 | 10/1998 |
| EP | 0 873 762 A3 | 6/1999 |
| EP | 0 968 732 A2 | 1/2000 |
| EP | 0 968 732 A3 | 1/2001 |
| EP | 0 873 762 B1 | 12/2003 |
| EP | 0 968 732 B1 | 9/2007 |
| WO | WO 98/21419 A1 | 5/1998 |
| WO | WO 2004/026373 A1 | 4/2004 |

OTHER PUBLICATIONS

"Porous Metal Products," Mott Corporation, Farmington, CT, available at least as early as Aug. 12, 2011; 16 pgs.

* cited by examiner

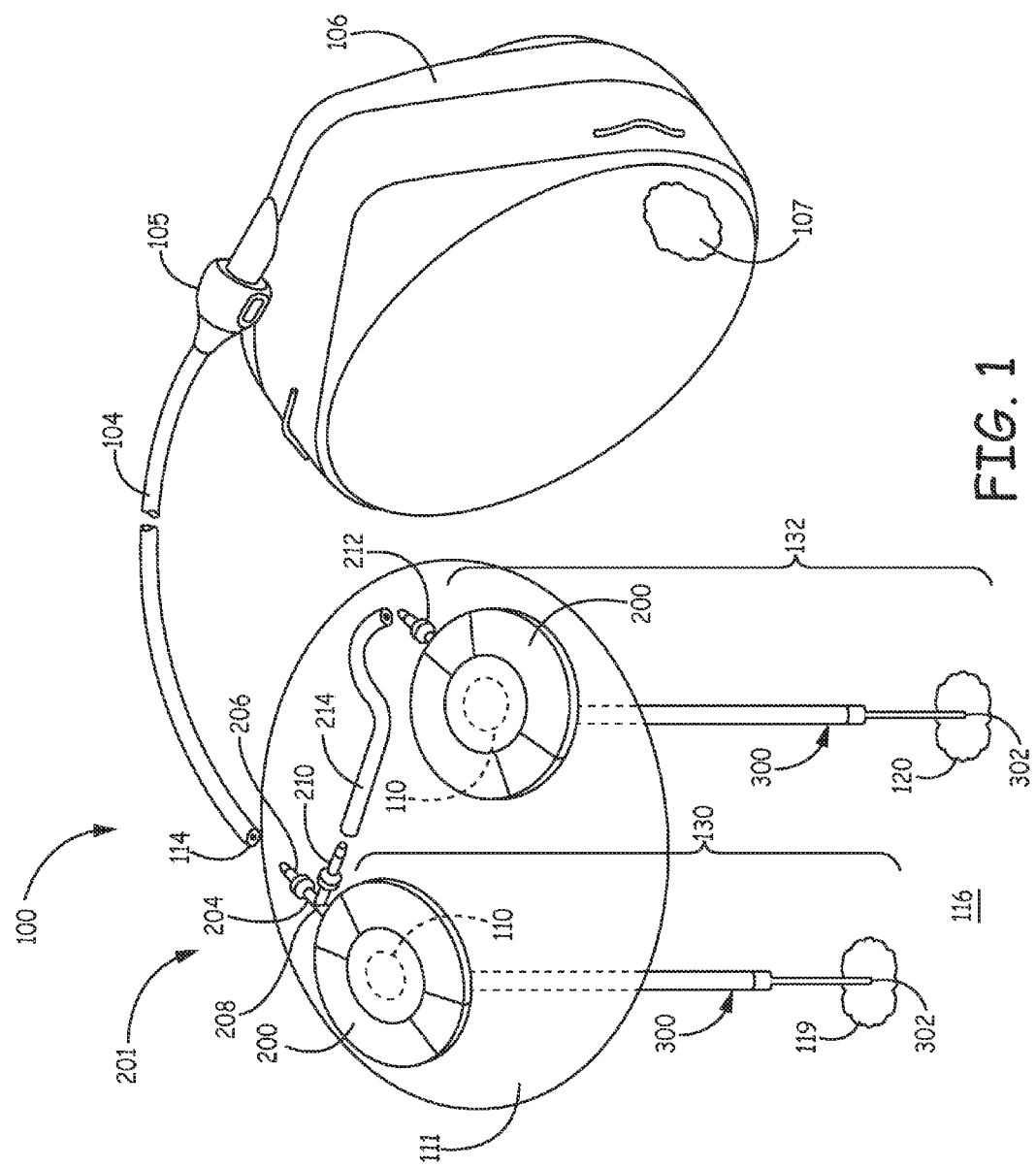

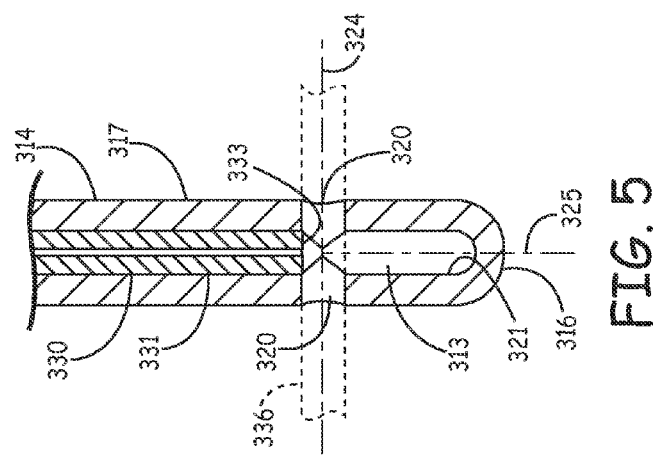
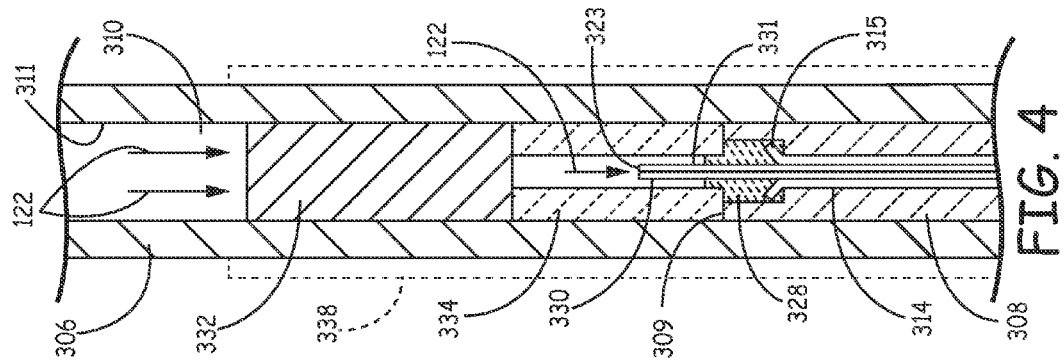
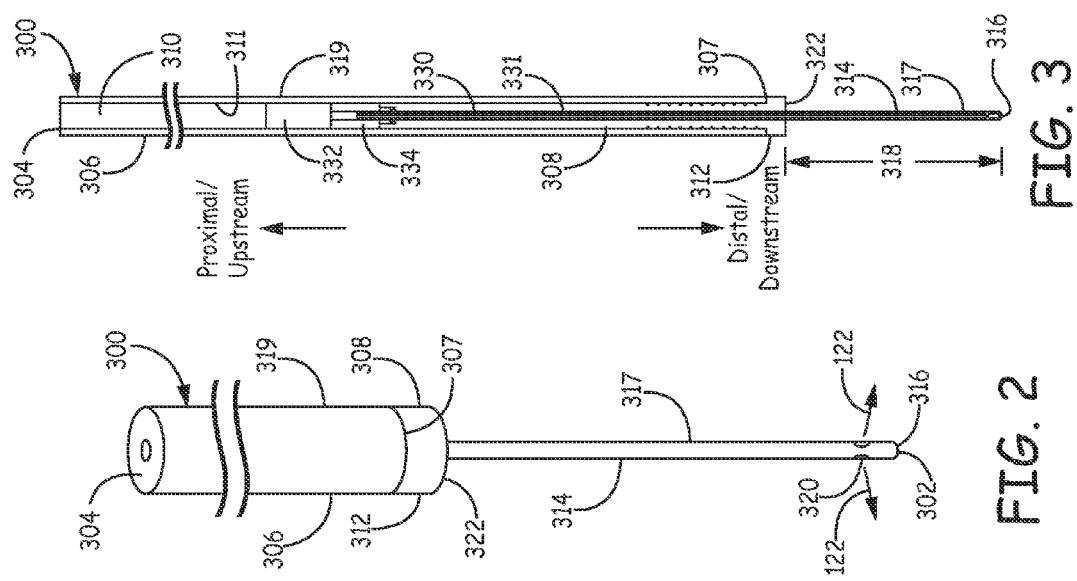

STEPPED CATHETERS WITH FLOW RESTRICTORS AND INFUSION SYSTEMS USING THE SAME

Embodiments of the present invention relate generally to implantable medical devices and, more particularly, to infusion systems incorporating two or more fluid delivery pathways, e.g., catheters, each containing one or more flow restrictors therein.

BACKGROUND

Implantable infusion systems are used to provide programmable long-term delivery of a therapeutic agent, e.g., infusate drug, to a target tissue location within, for example, the brain, spinal canal, or epidural space. These systems typically include a pump implanted at a remote location, e.g., within the abdominal or chest cavity, wherein the pump is connected to a catheter, the catheter having its distal end implanted at the target tissue location. In use, the therapeutic agent is delivered from a reservoir in the pump to the target tissue location via the catheter.

Some therapies, e.g., treatments of many neurological diseases, may benefit from infusion of a therapeutic agent to multiple locations within the body. For instance, for the treatment of Parkinson's disease, it may be beneficial to deliver a therapeutic agent, e.g., Glial Derived Neurotrophic Factor (GDNF), to both hemispheres of the brain (bilaterally). Infusing the therapeutic agent to such multiple target tissue locations can be accomplished by using multiple infusion systems, e.g., a separate pump and catheter with a single exit hole for each target tissue location. However, multiple systems result in not only increased costs and patient invasiveness (as compared to single target tissue location systems), but also increased complexity that is inherent in such multiple systems.

SUMMARY

Catheter systems and methods are described herein that incorporate flow restrictors to balance flow to multiple target tissue locations. Therapeutic agents may thus be delivered to the target tissue locations using multiple, separate therapy catheters connected to a single source containing the therapeutic agent.

In one embodiment, a catheter or catheter assembly is provided that includes a tubular catheter body having proximal and distal ends, wherein the body includes an inner surface defining a body lumen extending between the proximal and distal ends. A tubular needle is also provided and includes: a proximal portion fixed relative to the catheter body and located within the body lumen; and a protruding portion extending distally beyond the distal end of the catheter body, wherein the needle further comprises: an outer surface having a diameter that is less than a diameter of an outer surface of the catheter body; and an inner surface defining a needle lumen in fluid communication with the body lumen. A flow aperture in fluid communication with the needle lumen is provided along the protruding portion at or near a distal end of the needle. The catheter assembly may also include a flow restrictor located within the needle lumen and fixed in position relative to the needle, the flow restrictor having a distal end positioned at or near the flow aperture.

In another embodiment, a catheter assembly is provided that includes a flexible tubular catheter body having proximal and distal ends, the body having an inner surface defining a body lumen extending between the proximal and distal ends. A guide tube is also included and fixed to the inner surface of the body near the distal end of the body such that the guide tube is at least partially located within the body lumen, wherein the guide tube includes a distal end face positioned at or near the distal end of the body. A tubular needle is further provided and includes a proximal portion extending along an inner surface of the guide tube, and a protruding portion extending distally beyond the distal end face of the guide tube. The needle further includes: an outer surface having a diameter that is less than a diameter of an outer surface of the catheter body; and an inner surface defining a needle lumen in fluid communication with the body lumen, wherein a side flow aperture in fluid communication with the needle lumen is provided along the protruding portion near a distal end of the needle, wherein the side flow aperture defines a flow axis transverse to a longitudinal axis of the needle. An elongate flow restrictor is also provided and positioned within the needle, the flow restrictor having a proximal end and a distal end, the distal end located at or near the side flow aperture. A filter element is provided and located near the proximal end of the flow restrictor within the body lumen.

In yet another embodiment, an infusion catheter system is provided that includes: a first therapy catheter having a proximal end and a distal end, wherein the first therapy catheter defines a first lumen extending from the proximal end of the first therapy catheter to a flow aperture through which fluid flowing distally through the first lumen of the first therapy catheter from the proximal end exits the first therapy catheter; and a second therapy catheter comprising a proximal end and a distal end, wherein the second therapy catheter includes a second lumen extending from the proximal end of the second therapy catheter to a flow aperture through which fluid flowing distally through the second lumen from the proximal end of the second therapy catheter exits the second therapy catheter. The system further includes a flow splitter comprising: a supply port; a first exit port in fluid communication with the first lumen of the first therapy catheter; and a second exit port in fluid communication with the second lumen of the second therapy catheter, wherein fluid entering the flow splitter through the supply port exits the flow splitter through either the first exit port or the second exit port. The system also includes: a first flow restrictor located within the first lumen near the flow aperture of the first therapy catheter such that the fluid flowing through the first exit port into the first lumen passes through the first flow restrictor; and a second flow restrictor located within the second lumen near the flow aperture of the second therapy catheter such that the fluid flowing through the second exit port into the second lumen passes through the second flow restrictor. A burr hole anchor is provided and configured to secure to tissue at a cranial burr hole, wherein the anchor is configured to receive and immobilize the first therapy catheter as it passes through the burr hole.

The above summary is not intended to describe each embodiment or every implementation of the present invention. Rather, a more complete understanding of the invention will become apparent and appreciated by reference to the following Detailed Description of Exemplary Embodiments and claims in view of the accompanying figures of the drawing.

BRIEF DESCRIPTION OF THE VIEWS OF THE DRAWING

The present invention will be further described with reference to the figures of the drawing, wherein:

FIG. 1 diagrammatically illustrates a multi-site, e.g., two leg, implantable infusion system incorporating stepped (e.g., needle tip) catheter assemblies in accordance with embodiments of the present invention;

FIG. 2 is an enlarged perspective view of a needle tip catheter assembly in accordance with one embodiment of the invention;

FIG. 3 is a section view of a distal portion of the needle tip catheter assembly of FIG. 2 in accordance with one embodiment of the invention;

FIG. 4 is an enlarged section view of a portion of the catheter assembly of FIG. 3;

FIG. 5 is an enlarged section view of another portion of the catheter assembly of FIG. 3;

Figure 6:
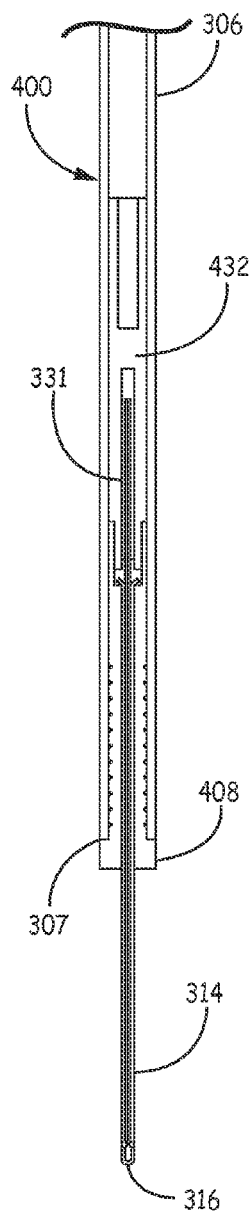
FIG. 6 is a section view of a distal portion of a needle tip catheter assembly in accordance with another embodiment of the invention.

The figures are rendered primarily for clarity and, as a result, are not necessarily drawn to scale. Moreover, various structure/components, including but not limited to fasteners, electrical components (wiring, cables, etc.), and the like, may be shown diagrammatically or removed from some or all of the views to better illustrate aspects of the depicted embodiments, or where inclusion of such structure/components is not necessary to an understanding of the various exemplary embodiments of the invention. The lack of illustration/description of such structure/components in a particular figure is, however, not to be interpreted as limiting the scope of the invention in any way.

DETAILED DESCRIPTION OF EXEMPLARY EMBODIMENTS

In the following detailed description of illustrative embodiments of the invention, reference is made to the accompanying figures of the drawing which form a part hereof, and in which are shown, by way of illustration, specific embodiments in which the invention may be practiced. It is to be understood that other embodiments may be utilized and structural changes may be made without departing from the scope of the present invention.

Embodiments of the present invention are directed generally to fluid conduits such as infusion catheter assemblies (also referred to herein as "catheters") and to catheter systems, infusion systems, and methods using the same. For example, embodiments of the present invention may include a therapy tube, e.g., an intraparenchymal (IPA) therapy catheter, for delivering a fluid (e.g., therapeutic agent) to a target tissue location within a human or other mammalian body.

While embodiments of the present invention may find application to a variety of catheters/catheter systems, they may be particularly advantageous when utilized with stepped or "needle tip" catheter configurations. Such catheters may reduce backflow of the therapeutic agent along the catheter trajectory, thus increasing the chances that the desired quantity of the therapeutic agent is dispersed at the target tissue location.

Backflow (also referred to as "reflux") may occur along an implanted catheter when a fluidic seal between the catheter and surrounding tissue (e.g., brain) is broken (for additional information, see U.S. Pat. App. Pub. No. 2009/0143764 to Nelson). Although somewhat difficult to measure directly, backflow may be detected by observation of fluid dispersion under, for example, magnetic resonance imaging (MRI). While backflow may occur with many delivery techniques, it may be particularly problematic during convection enhanced delivery (CED) to the brain. Convection enhanced delivery to the brain uses bulk flow in extracellular space resulting from a pressure gradient. Such flow may significantly enhance tissue penetration of the delivered therapeutic agent.

In some instances, CED (as well as other treatments) may benefit from delivery of the therapeutic agent to two or more discrete target tissue locations. A potential benefit of catheter assemblies and flow restrictors in accordance with embodiments of the present invention is that the therapeutic agent may be delivered from a single infusion source to these two or more distinct locations (e.g., bilateral infusion). For example, catheter systems in accordance with embodiments of the instant invention may branch or divide flow (e.g., provided by the infusion source through a first or delivery catheter) to two or more legs formed by secondary or therapy catheters, thus producing a bifurcated catheter system. Stated alternatively, a single infusion pump may be used to deliver one or more therapeutic agents to multiple locations within a body. To provide substantially equal flow to each therapy catheter, embodiments as described herein may provide a flow resistor limiting flow through each leg of the system. Although the exemplary flow restrictors described and illustrated herein may be used in an attempt to equalize flow rates through the different legs of a branched catheter system, flow restrictors in accordance with embodiments of the present invention may, in some instances, alternatively provide different flow rates through the different legs by varying the flow restriction provided by the different flow restrictors.

As used herein, the term "flow restrictor" refers to a flow resistance that is added to a system to bring the total resistance to a specified value; it does not necessarily refer to a singular component. For example, two "flow restrictors" (i.e. two components) of equal resistance placed in series could be functionally equivalent to a single flow restrictor whose resistance is twice that of either of the series restrictors taken by itself.

As used herein, "therapeutic agents" may be a generic term referring to a fluid containing pharmaceutical compositions, genetic materials, biologics, and other substances. Pharmaceutical compositions may include, for example, antispasmodics, pain medications, chemotherapeutic agents, and the like. Genetic materials include substances intended to have a direct or indirect genetic therapeutic effect such as genetic vectors, genetic regulator elements, genetic structural elements, DNA, and the like. Biologics include substances that are living matter or derived from living matter intended to have a therapeutic effect such as stem cells, platelets, hormones, biologically produced chemicals, and the like. Other substances may include those that do not have a direct therapeutic effect such as, saline solutions, fluoroscopy agents, disease diagnostic agents, and the like. Accordingly, unless otherwise noted, the terms "therapeutic agent," "therapeutic substance," "drug," or "fluid" may be used interchangeably herein and may include most any therapeutic, diagnostic, or other substance that is delivered using the implantable systems and methods described herein.

It is noted that the terms "comprises" and variations thereof do not have a limiting meaning where these terms appear in the accompanying description and claims. Further, "a," "an," "the," "at least one," and "one or more" are used interchangeably herein. Moreover, relative terms such as "left," "right," "front," forward," "aft," "rear," "rearward," "top," "bottom," "side," "upper," "lower," "above," "below," "horizontal," "vertical," and the like may be used herein and, if so, are from the perspective observed in the particular figure. These terms are used only to simplify the description, however, and not to limit the scope of the invention in any way.

For simplicity, many components (e.g., tubes/catheters, flow restrictors, capillary tubes, lumens or fluid pathways, etc.) are described and illustrated herein as being generally cylindrical in shape (e.g., of circular cross section). However, this configuration is not limiting, and embodiments having different shapes are certainly possible without departing from the scope of the invention. For example, catheters and flow restrictors described herein could alternatively include cross-sectional profiles (in addition to circular) that are triangular, oval, elliptical, hexagonal, semi-circular, etc. Further, the term "diameter" may refer to the greatest cross-sectional dimension taken perpendicular to a longitudinal axis of the component, whether it has a circular or non-circular cross-sectional shape.

As used herein, the term "fixed" refers to attachment of two components via most any acceptable method that fixes or immobilizes the two components relative to one another such that the two components function as an integral component (e.g., one component is restricted from movement relative to the other). Fixing could be achieved, for example, by staking, bonding, reflowing, adhering, heat-shrinking, interference-fitting, press-fitting, etc.

With reference to the drawing, wherein like reference numerals designate like parts and assemblies throughout the several views, FIG. 1 diagrammatically illustrates an exemplary implantable medical system such as a brain infusion system 100 as it may be configured during use, e.g., implantation. Exemplary embodiments of the components described and illustrated herein may be sized for use with burr holes typical in human and other mammalian (e.g., primate) applications (e.g., about 6 millimeters (mm) to about 14 mm in diameter). However, such a configuration is not limiting as exemplary anchors could be scaled to accommodate most any size burr hole without departing from the scope of the invention. Moreover, while described herein with respect to burr hole access (i.e., intracranial implants), embodiments of the present invention may also find use in other body portal applications.

The exemplary infusion system 100 may branch or split flow into two legs identified herein as first leg 130 and second leg 132 (although additional legs are also possible). The system 100 may include a therapy source 106 and a catheter system, e.g., ant-backflow infusion catheter system 201. Further included, for each leg 130 and 132, is a cranial burr hole anchor device (each referred to herein as "anchor 200") and a first medical tube (e.g., an intra-cranial IPA catheter) identified herein as a therapy catheter or catheter assembly 300. Each therapy catheter 300 may be partially implanted within a mammalian (e.g., human) brain 116 such that a distal end (therapy delivery tip 302) is located at a target tissue location (location 119 for the first leg 130 and location 120 for the second leg 132) in the brain. The prefixes "first" and "second" may be used herein to describe substantially similar components/aspects associated with the first leg 130 and the second leg 132, respectively. These terms are used for convenience only, and are not intended to limit the scope of the invention in any way.

To assist with placement of each therapy catheter 300, a stereotactic apparatus (not shown) may be utilized (see, for example, U.S. Pat. App. Pub. No. 2012/0083742 to Nelson).

In the illustrated example, each therapy catheter 300 is implanted through a body portal, e.g., through a burr hole 110 (the burr holes covered by the anchors 200 in FIG. 1). Each burr hole 110 may be formed in tissue (e.g., the bone forming the skull 111) in accordance with known techniques. Each anchor 200 may be configured to secure to the tissue at or around the burr hole 110 and receive and immobilize the respective catheter 300 passing through the burr hole/anchor.

Once each therapy catheter 300 is accurately implanted through the burr hole (i.e., once the therapy delivery tips 302 are positioned at the predetermined target tissue locations 119 and 120 in the brain 116), a proximal or first end 304 (see FIGS. 2 and 3) of each therapy catheter 300 may be routable through its respective anchor 200. In the illustrated embodiment, the first end 304 of the first therapy catheter 300 of the first leg 130 (after disconnecting from the stereotactic apparatus and trimming to an appropriate length) may be operatively connected to a corresponding first end 114 of a feed or delivery catheter 104. In the illustrated embodiment, an intermediate connector or flow splitter 204 may be provided that includes a supply port 206 for fluidly coupling to the first end 114 of the delivery catheter 104. The connector 204 may also include a first exit port 208 fluidly communicating with a lumen of the first therapy catheter 300 (of the first leg 130) and a second exit port 210 fluidly communicating with a lumen of the second therapy catheter 300 (of the second leg 132). In use, fluid entering the flow splitter 204 through the supply port 206 may exit the flow splitter through either the first exit port 208 or the second exit port 210. The first exit port 208 may extend into the respective anchor 200 where it may fluidly connect to the first or proximal end 304 (see FIG. 2) of the first therapy catheter 300 of the first leg 130. The second therapy catheter 300 of the second leg 132 may fluidly couple to the second exit port 210, e.g., via a connector 212 provided on the anchor 200 of the second leg (and to which the first or proximal end 304 of the second therapy catheter 300 is connected) and a connecting catheter 214 as shown in FIG. 1.

The delivery catheter 104 may have a second end 105 configured to couple to the therapy source or reservoir (e.g., an implantable infusion pump 106 having an internal reservoir 107 such as a SynchroMed® II programmable infusion pump distributed by Medtronic, Inc., of Minneapolis, Minn. USA) containing a volume of the therapeutic agent. As a result, the infusion pump may fluidly couple to the supply port 206 such that fluid contained in the pump is deliverable to lumens and flow apertures of the first and second therapy catheters 300. The pump 106 may be implanted at another location, e.g., within the chest or abdominal cavity. While described and illustrated herein utilizing an implantable infusion pump, this configuration is not limiting. For example, other embodiments may replace the pump with most any internal or external medicament delivery device, e.g., syringe, drip bag, etc.

The infusion system 100 may, in one embodiment, be configured to deliver a therapeutic agent for the treatment of a chronic ailment, e.g., CED of a therapeutic agent for the treatment of Huntington's disease. Accordingly, catheters and systems in accordance with embodiments of the present invention may be implanted for long periods of time (e.g., seven years or more). This application is not limiting, however, as the system may be configured to deliver other therapeutic agents (e.g., such as for the treatment of Parkinson's or Alzheimer's disease) to the brain or to most any other region of the body.

As shown in FIG. 1, the pump 106 may simultaneously deliver the therapeutic substance contained therein to both: the target tissue location 119 e.g., via the delivery catheter 104, supply port 206, first exit port 208, and first therapy catheter 300 of the first leg 130; and the target tissue location 120 e.g., via the delivery catheter 104, supply port 206, second exit port 210, connecting catheter 214, connector 212, and the second therapy catheter 300 of the second leg 132.

To ensure the desired flow is delivered to both the target tissue locations 119 and 120, the system 100 may include flow restrictors in both the first and second legs 130, 132. Embodiments of the present invention may provide such flow restrictors directly within each therapy catheter 300 as further described below. That is, a first flow restrictor may be provided and located within a lumen and near a distal flow aperture of the first therapy catheter (of the first leg 130), and a second flow restrictor may be provided and located within a lumen and near a distal flow aperture of the second therapy catheter (of the second leg 132). Accordingly, fluid flowing through the first exit port 208 of the connector 204 flows through the lumen of the first therapy catheter and through the first flow restrictor, while fluid flowing through the second exit port 210 flows through the lumen of the second therapy catheter and through the second flow restrictor.

FIG. 2 illustrates one of the exemplary catheters 300 of FIG. 1 that may be used to distribute the therapeutic agent to a location within a body, e.g., within the brain. Some aspects of the catheter 300 are similar to catheters described in U.S. Pat. App. Pub. No. 2009-0143764 to Nelson. However, the catheter 300 may incorporate additional and/or different features including flow restriction and filtration as further described herein.

FIGS. 3-5 illustrate an internal construction of the catheter 300 in accordance with one embodiment of the invention. As shown in these figures, each catheter 300 may include a tubular catheter body 306, which may be constructed of a flexible material such as urethane, having a first or proximal end 304 and a second or distal end 307, wherein the body includes an inner surface 311 defining a body lumen 310 extending between the proximal and distal ends.

As shown in FIG. 3, an annular guide tube 308 may be fixed to the body (e.g., to the inner surface 311 of the body 306) near the distal end 307 such that the guide tube is at least partially located within the body lumen 310. The guide tube 308 may further include a distal end face 322 positioned at or near the distal end 307 of the body 306. A distal end of the guide tube 308 may, in some embodiments, form a flange or flange portion 312 that abuts the distal end 307 of the body 306 when the guide tube 308 is fully inserted therein as shown in FIGS. 2 and 3.

A preferably rigid tubular tip member may be partially located within the body 306 and extend outwardly from the distal end 307 and the flange 312. In some embodiments, the tip member forms a reduced diameter portion or section, e.g., tubular needle 314. The needle 314 may include a proximal portion fixed relative to the catheter body 306 and located within the body lumen 310. For instance, the proximal portion may extend along the guide tube 308 (e.g., extend along an inner surface of the guide tube). The needle may also include a protruding portion extending distally beyond the distal end 307 of the catheter body, e.g., beyond the distal end face 322 of the guide tube, as illustrated in FIGS. 2 and 3. In one embodiment, the needle 314, e.g., a distal end or tip 316 of the needle, is configured to extend a preset distance 318 (which, in one embodiment, may be about 0.2 to about 0.4 inches) beyond the distal end face 322 of the guide tube (alternatively, the preset distance could be measured beyond the distal end 307 of the body 306) such that the catheter 300 defines what is herein referred to as a stepped or needle tip catheter providing a reduced diameter portion.

The needle 314 may include: an outer surface 317 having a diameter that is less than a diameter of an outer surface 319 of the catheter body 306; and an inner surface 321 (see FIG. 5) defining a needle lumen 313 in fluid communication with the body lumen 310 (e.g., fluid flowing through the body lumen may ultimately enter the needle lumen). In addition to reduced coring, the relatively smaller (compared to the catheter body) diameter of the protruding needle 314 minimizes the diameter of the most distal portion of the catheter 300, which may reduce tissue trauma during catheter introduction. The smaller diameter of the needle 314 may further contribute to reduced backflow (see, e.g., US 2009-0143764).

The distal end 316 of the needle 314 (which forms the most-distal end 302 of the catheter 300) may, in one embodiment, be sealed or closed (e.g., form a sealed distal tip) as shown in FIG. 5. Such a configuration may also assist in reducing coring and tissue trauma during catheter introduction. While axial closure of the distal tip 316 restricts axial flow from the needle tip, one or more flow apertures 320 (e.g., two diametrically opposed flow apertures as shown) may be provided in fluid communication with the needle lumen 313, e.g., at a location along the protruding portion at or near the distal end 302 (e.g., proximate to, but offset from, the sealed distal tip 316). In one embodiment, the flow apertures 320 may each include an axis that forms an angle with a longitudinal axis of the catheter body/needle. For instance, one or more apertures 320 could be configured as side flow apertures, each having an axis 324 that forms an angle of about 90 degrees with a longitudinal axis 325 of the needle/catheter body as shown in FIG. 5. Stated alternatively, the flow apertures may define a flow axis 324 transverse to the longitudinal axis 325 of the needle 314. Once again, these flow apertures 320 are fluidly coupled to the lumen 310 of the catheter body (via the needle lumen 313) so that therapeutic agent 122 flowing through the lumen 310 may pass into the needle lumen 313 and out through the aperture(s) 320 as indicated in FIGS. 2 and 4.

Due to the stepped construction of the catheter 300, an obstructive element or ledge, e.g., formed by the distal end face 322, may be provided and positioned along the catheter and spaced-apart from the distal tip (e.g., from the flow apertures) by the preset distance 318. The distal end face 322 may, in one embodiment, be formed by the flange 312 of the guide tube 308. The ledge 322 may form a barrier capable of reducing backflow of the therapeutic substance delivered by the catheter 300.

While not wishing to be bound to any particular configuration, the catheter body 306 may, in one embodiment, be made from a flexible and shearable (trimmable) material such as 55D urethane tubing and have an inner surface 311 defined by an inner diameter of about 0.024 inches (in) and an outer surface 319 defined by an outer diameter of about 0.041 in. While described as urethane, the catheter body 206 may be made from other materials such as other urethanes, silicones, and blends of the same. In yet other embodiments, the catheter body could be made from more rigid materials.

The guide tube 308 may, in one embodiment, be made from a relatively rigid material, e.g., polyetheretherketone (PEEK) or 316 stainless steel. In the illustrated embodiment, the guide tube may have a length (including the flange 312)

of about 0.2 in to about 0.5 in, e.g., about 0.4 in. However, relative size of the guide tube, as well as the other components of the catheter, may be adapted to suite most any particular application.

The needle 314 may, in one embodiment, be made from 316 stainless steel hypodermic tubing and have a proximal end 315 (see FIG. 4) that is fixed, when assembled, at a location within the lumen 310 of the body 306 and located at or near a proximal end 309 of the guide tube 308. Alternatively, the needle 314 may be 80/20 Platinum/Iridium hypodermic tubing, which allows the needle to be seen clearly during magnetic resonance imaging (MRI)). The inner surface 321 of the needle 314 (see FIG. 5) may have an inner diameter of about 0.004 in, and the outer surface 317 may have an outer diameter of about 0.006 in to about 0.010 in, e.g., about 0.008 in (e.g., a 33 gage needle). Accordingly, the outer diameter (of the outer surface 317) of the needle 314 is less than the outer diameter (of the outer surface 319) of the body 306 to yield the desired stepped configuration. In the illustrated embodiment, each of the aligned flow apertures 320 may have a diameter of about 0.004 in.

The needle 314 may, in one embodiment, be fixed to the guide tube 308 via a heat-staking process. Alternatively, the needle could be attached with a cyanoacrylate adhesive. In still yet other embodiments, the needle could be overmolded with the guide tube 308, or fixed in accordance with other accepted methods.

Referring to FIGS. 3-5, an embodiment of the catheter 300 incorporating a flow restrictor 330 within the needle 314 in accordance with one embodiment of the invention will now be described. As shown in FIGS. 3 and 4, the flow restrictor 330 may be configured as a cylindrical, elongate capillary 331 or capillary tube located within the reduced diameter portion of the catheter, e.g., located within the needle lumen 313 of the needle 314, and fixed in position relative to the needle as best illustrated in FIG. 4. For example, in one embodiment, the flow restrictor (e.g., capillary 331) may be fixed to one or both of the needle and the guide tube. While not wishing to be bound to any particular configuration, the capillary 331 may be a TSP model fused silica capillary distributed by Polymicro Technologies of Phoenix, Ariz., USA. The capillary may include a polyimide coating and have an inner diameter of about 10 to about 20 microns, an outer diameter of about 90 to about 100 microns, and a length of about 0.5 in. Once again, such parameters are illustrative only as different configurations may be provided to yield different flow resistances.

To prevent occlusion of the small flow channel (e.g., inner diameter) provided by the capillary 331, a filter element or filter 332 may also be provided. In the illustrated embodiment, the filter 332 may be a sintered Titanium cylindrical filter providing filtration of particles greater than 0.2 microns in size. Such filters are available from, for example, Mott Corporation of Farmington, Conn., USA. As shown in FIG. 4, the filter 332 may be positioned within the body lumen 310 (e.g., fixed to the body 306) between the proximal end 304 of the body and the flow restrictor 330. That is, the filter 332 may be positioned at or near (and upstream from) a proximal end 323 of the capillary to ensure that debris capable of clogging the capillary 331 are effectively blocked by the filter. To provide adequate space between the filter 332 and the capillary 331, a tubular sleeve 334 (which may be made of PEEK or a similar biocompatible material) may be provided and positioned between the flow restrictor and the filter. As FIG. 4 illustrates, the sleeve permits the filter 332 to be spaced-apart from the flow restrictor, thereby providing a suitable volume for therapeutic substance 122 that has passed through the filter 332 before entering the capillary 331.

As used herein, "proximal" is understood to indicate that portion or direction of the catheter 300 closer to the first end 304, while "distal" is understood to indicate portions or directions more toward the second end 302 of the catheter. Similarly, the term "upstream" is understood to refer to the direction closer toward the source of the flow of therapeutic agent (e.g., the proximal end 304 of the catheter), while the term "downstream" is understood to refer to the direction closer toward flow output of the system, e.g., closer to the flow apertures 320.

To assemble the exemplary catheter 300 of FIGS. 3-5, the needle 314 may be inserted, distal end 316 first, into the proximal end 309 of the guide tube 308. The proximal end 315 of the needle 314 may be flared or flanged as shown in FIG. 4. The flange may captivate the needle (e.g., prevent the needle from exiting the distal end of the guide tube 308) in the event that the fixation (e.g., heat stake) between the needle and the guide tube fails. The proximal end 309 of the guide tube 308 may optionally be relieved or counterbored to assist with accommodating the flare of the proximal end 315 of the needle.

The capillary 331 may then be inserted into the needle lumen 313. To ensure that the capillary, e.g., a distal end 333 of the capillary 331 (see FIG. 5), is positioned at or near (and upstream from) the flow apertures 320, a cylindrical member 336 (e.g., a separate piece of capillary tubing) may be inserted into the opposing flow apertures 320 of the needle. The capillary 331 may then be inserted, distal end 333 first, into the proximal end 315 of the needle 314 until the distal end 333 is at or near the flow apertures 320, e.g., until the distal end of the capillary rests against the cylindrical member 336. Preferably, the flow restrictor 330 does not extend into the flow aperture 320 where it could interfere with flow of the therapeutic substance (e.g., the distal end 333 of the capillary 331 is preferably located at, or upstream of the most upstream edge of the flow apertures as shown in FIG. 5). As stated elsewhere herein, the rigidity of the needle 314 and guide tube 308 may protect the potentially delicate capillary 331.

An adhesive 328 (see FIG. 4) may then be applied to the proximal end 309 of the guide tube 308 (e.g., dispensed into the counterbore formed at the first end 309 of the guide tube). Some adhesive 328 may flow into the annular region formed between the capillary 331 and the lumen 313 of the needle 314 (as well as into the region between the needle and the lumen of the guide tube), effectively sealing any alternative flow path around the capillary. The sleeve 334 may then be attached, via the adhesive 328, to the end of the guide tube 308.

The filter 332, sleeve 334, and the needle 314/capillary 331 may then be inserted into the distal end 307 (see FIG. 3) of the catheter body 306. After adjusting the locations of each component relative to one another, a piece of shrink wrap tubing 338 may be slid over the catheter body 306 as shown in FIG. 4. The entire assembly may then be heated to a temperature appropriate to reflow the urethane catheter body 306. As the catheter body 306 reflows, the shrink wrap tubing contracts. As a result, the catheter body 306 reflow bonds to the guide tube 308, the sleeve, 334, and the filter 332, effectively immobilizing or fixing all these components of the catheter 300 relative to the inner surface of the catheter body and sealing alternative flow pathways that could bypass the filter and the capillary. After cooling, the shrink wrap tubing 338 may be slit and removed, and the cylindrical member 336 (see FIG. 5) removed.

In embodiments wherein the catheter body is formed of a thermoset material (e.g., silicone or another material that cannot be reflowed), an adhesive could be used to both: adhere the various components (e.g., guide tube 308, sleeve 334, and filter 332) to the catheter body; and to seal off any alternative flow paths that could bypass the capillary.

While described and illustrated herein as incorporating the guide tube 308, its inclusion with the catheter 300 may be optional. For example, the catheter 300 could be configured with an inner diameter (e.g., diameter of the inner surface 311) approximately equal to an outer diameter (e.g., diameter of the outer surface 317) of the needle 314. As a result, reflowing the catheter body 306 could then fix the needle directly to the body (e.g., by positively retaining the flange at the proximal end 315 of the catheter (see FIG. 4)). In this configuration, the distal end 307 of the body would form the step of the catheter, and the preset distance 318 would be measured from the distal end 307.

Figure 7:
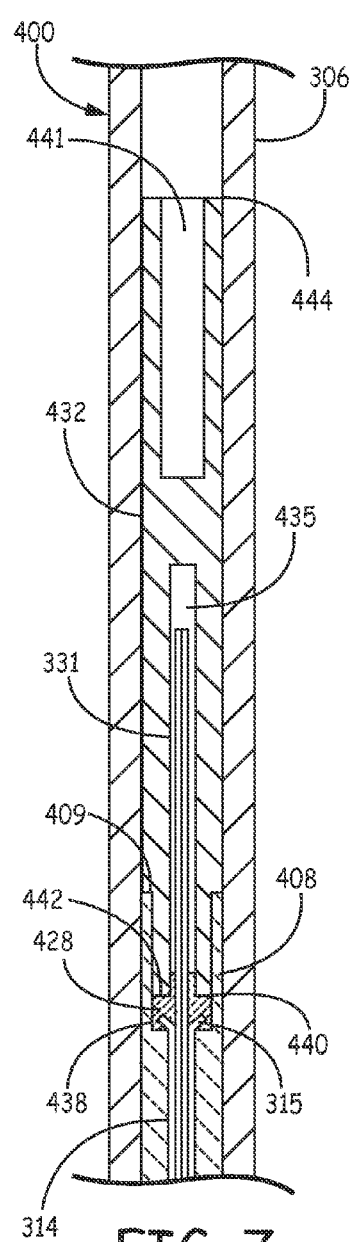
FIG. 7 is an enlarged section view of a portion of the catheter assembly of FIG. 6.
Figure 8:
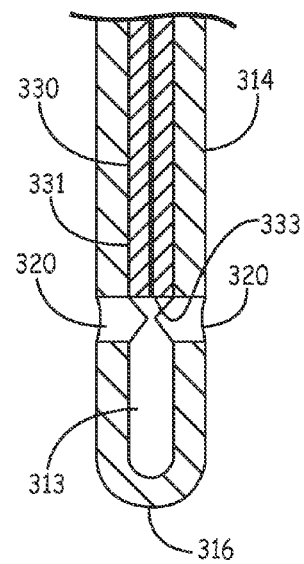
FIG. 8 is an enlarged section view of another portion of the catheter assembly of FIG. 6.

FIGS. 6-8 illustrate a therapy catheter (or catheter assembly) 400 in accordance with another embodiment of the invention. Externally, the therapy catheter 400 may appear identical to the catheter 300. Accordingly, only those aspects of the therapy catheter 400 that are different than the therapy catheter 300 will be described, with the understanding that the catheter 400 is otherwise identical to the catheter 300 and the two (or aspects of the two) may be substituted for one another (e.g., the catheter 400 could be substituted in FIG. 1 for one or both of the catheters 300) without departing from the scope of the invention.

As shown in FIGS. 6-8, the catheter 400 again includes the catheter body 306, capillary 331, and needle 314 configured substantially as described above. The catheter 400 may further include a guide tube 408 and a filter 432 in accordance with other embodiments of the invention.

As shown in FIG. 6, the guide tube 408 may be similar to the guide tube 308 in most ways. It may differ, however, by including a deeper, counterbored well 440 at its proximal end 409 as shown also in FIG. 7. The well 440 is provided to receive both a volume of adhesive 428 as further described below, as well as a distal end 442 of the filter 432.

The filter 432 may be constructed from a similar material (e.g., sintered Titanium) as the filter 331. However, a proximal or upstream end 444 of the filter 432 may also include a counterbored well 441 as shown in FIG. 7. The well 441 may provide increased filtering surface area, reducing potential occlusion of the catheter 400/system 100. The distal end 442 of the filter 432 may also neck down to a reduced diameter configured to engage or pilot into the well 440 of the proximal end 409 of the guide tube 408. By receiving the distal end 442 of the filter 432 within the guide tube 408, the filter may be fixed to the guide tube. As a result, increased structural rigidity of the connected components may be realized, offering desirable protection to the capillary 331.

In one embodiment, the catheter 400 may be assembled by first inserting the needle 314, distal end 316 first, into the proximal end 409 of the guide tube 408, after which the needle 314 may be heat staked to the guide tube. The capillary 331 may then be inserted into the proximal end 315 of the needle 314. The capillary 331 may be located within the guide tube using the same process already described herein (e.g., indexing off of a cylindrical member 336 such as that described with reference to FIG. 5). Alternatively, the capillary 331 could be located such that its distal end 333 is slightly offset, e.g., in the upstream direction, from the flow apertures 320.

The filter 432 may then be inserted such that the capillary 331 is received within a counterbored well or pilot hole 435 formed in the second or distal end 442 of the filter. Prior to inserting the distal end 442 of the filter 332 into the well 440 of the guide tube 408, a volume of adhesive 428 may be placed on the exterior surface of the distal end 442 and in the well 440. The filter 432 may then be fully inserted into the well 411 as shown in FIG. 7. When fully inserted, a gap 438 may still exist to accommodate the adhesive 428 as also shown in FIG. 7. Once again, the adhesive may secure the various components to one another, and may further seal alternative flow paths that could permit the therapeutic substance to bypass the capillary 331.

At this point, the assembly (filter, guide tube, capillary, and needle) may be inserted into the distal end 307 of the catheter body 306 and the catheter body reflowed in a manner described above with reference to the catheter body 306.

Once again, while identified herein with some degree of specificity, the sizes, materials, and geometry of various components are understood to be exemplary only and other sizes, materials, and geometries are certainly possible without departing from the scope of the invention.

As one of skill in the art may recognize, housing the flow restrictor in the reduced diameter portion or needle provides numerous benefits. For example, such a configuration negates the need for accommodating the flow restrictor elsewhere, e.g., in the anchor itself, potentially simplifying the infusion/catheter system. In addition, the rigidity of the needle 314 and guide tube 308 may prevent excessive bending in the vicinity of the needle, thereby providing protection to the potentially delicate fused silica capillary 331. Further, by locating the capillary 331 in close proximity to the flow aperture (e.g., 320), the capillary may reduce or even prevent potentially flow-blocking contaminants (e.g., blood that subsequently clots) from entering the catheter (e.g., via the apertures 320). Moreover, the simple cylindrical capillary tube is readily available and cost-effective as compared to more complicated flow restrictor configurations. Still further, while the capillaries in each leg of system may be flow-matched to produce the same flow resistance, other embodiments may provide different restrictors in different legs without departing from the scope of the invention.

The complete disclosure of the patents, patent documents, and publications cited in the Background, the Detailed Description of Exemplary Embodiments, and elsewhere herein are incorporated by reference in their entirety as if each were individually incorporated.

Illustrative embodiments of this invention are described and reference has been made to possible variations within the scope of this invention. These and other variations, combinations, and modifications of the invention will be apparent to those skilled in the art without departing from the scope of the invention, and it should be understood that this invention is not limited to the illustrative embodiments set forth herein. Accordingly, the invention is to be limited only by the claims provided below and equivalents thereof.

What is claimed is:

1. A catheter assembly, comprising:
   a tubular catheter body having proximal and distal ends, the body comprising an inner surface defining a body lumen extending between the proximal and distal ends;
   a tubular needle comprising a proximal portion fixed relative to the catheter body and located within the body lumen, and a protruding portion extending distally beyond the distal end of the catheter body, wherein the needle further comprises: an outer surface having a diameter that is less than a diameter of an outer surface of the catheter body; and an inner surface defining a needle lumen in fluid communication with the body lumen, wherein a flow aperture in fluid communication with the needle lumen is provided along the protruding portion at or near a distal end of the needle;
- a flow restrictor located within the needle lumen and fixed in position relative to the needle, the flow restrictor comprising a distal end positioned at or near the flow aperture;
- a filter element positioned within the body lumen at or near a proximal end of the flow restrictor; and
- a tubular sleeve positioned between the flow restrictor and the filter element.

2. The catheter assembly of claim 1, further comprising a guide tube fixed to the inner surface of the catheter body near the distal end of the catheter body such that the guide tube is at least partially located within the body lumen, the guide tube comprising a distal end face positioned at or near the distal end of the catheter body, and wherein the needle is fixed to the guide tube.

3. The catheter assembly of claim 1, wherein the distal end of the needle comprises a sealed distal tip, and wherein the flow aperture is located proximate to, but offset from, the sealed distal tip.

4. The catheter assembly of claim 1, wherein the flow restrictor is fixed to the needle.

5. The catheter assembly of claim 1, wherein the flow restrictor comprises a fused silica capillary.

6. The catheter assembly of claim 5, wherein the fused silica capillary is positioned such that a distal end of the capillary is at or near, and upstream from, the flow aperture.

7. The catheter assembly of claim 1, wherein the filter element is fixed to the inner surface of the catheter body.

8. The catheter assembly of claim 1, wherein the filter element comprises sintered Titanium.

9. The catheter assembly of claim 1, wherein an upstream end of the filter element defines a counterbored well.

10. A catheter assembly, comprising:
- a flexible tubular catheter body having proximal and distal ends, the body comprising an inner surface defining a body lumen extending between the proximal and distal ends;
- a guide tube fixed to the inner surface of the body near the distal end of the body such that the guide tube is at least partially located within the body lumen, the guide tube comprising a distal end face positioned at or near the distal end of the body;
- a tubular needle comprising a proximal portion extending along an inner surface of the guide tube, and a protruding portion extending distally beyond the distal end face of the guide tube, wherein the needle further comprises: an outer surface having a diameter that is less than a diameter of an outer surface of the catheter body; and an inner surface defining a needle lumen in fluid communication with the body lumen, wherein a side flow aperture in fluid communication with the needle lumen is provided along the protruding portion near a distal end of the needle, the side flow aperture defining a flow axis transverse to a longitudinal axis of the needle;
- an elongate flow restrictor positioned within the needle, the flow restrictor comprising a proximal end and a distal end, the distal end located at or near the side flow aperture;
- a filter element located near the proximal end of the flow restrictor within the body lumen; and
- a tubular sleeve positioned between the flow restrictor and the filter element.

11. The catheter assembly of claim 10, wherein the flow restrictor is fixed to one or both of the guide tube and the needle.

12. The catheter assembly of claim 10, wherein the filter element is fixed to the catheter body.

13. The catheter assembly of claim 10, wherein the flow restrictor comprises a fused silica capillary.

14. The catheter assembly of claim 10, wherein the filter element is spaced-apart from the flow restrictor.

15. An infusion catheter system comprising:
- a first therapy catheter comprising a proximal end and a distal end, wherein the first therapy catheter defines a first lumen extending from the proximal end of the first therapy catheter to a flow aperture through which fluid flowing distally through the first lumen of the first therapy catheter from the proximal end exits the first therapy catheter;
- a second therapy catheter comprising a proximal end and a distal end, wherein the second therapy catheter comprises a second lumen extending from the proximal end of the second therapy catheter to a flow aperture through which fluid flowing distally through the second lumen from the proximal end of the second therapy catheter exits the second therapy catheter;
- a flow splitter comprising: a supply port; a first exit port in fluid communication with the first lumen of the first therapy catheter; and a second exit port in fluid communication with the second lumen of the second therapy catheter, wherein fluid entering the flow splitter through the supply port exits the flow splitter through either the first exit port or the second exit port;
- a first flow restrictor located within the first lumen near the flow aperture of the first therapy catheter such that the fluid flowing through the first exit port into the first lumen passes through the first flow restrictor;
- a second flow restrictor located within the second lumen near the flow aperture of the second therapy catheter such that the fluid flowing through the second exit port into the second lumen passes through the second flow restrictor;
- a first filter element positioned within the first lumen between the proximal end of the first therapy catheter and the first flow restrictor;
- a second filter element positioned within the second lumen between the proximal end of the second therapy catheter and the second flow restrictor;
- a first tubular sleeve positioned between the first flow restrictor and the first filter element;
- a second tubular sleeve positioned between the second flow restrictor and the second filter element; and
- a burr hole anchor configured to secure to tissue at a cranial burr hole, wherein the anchor is configured to receive and immobilize the first therapy catheter as it passes through the burr hole.

16. The system of claim 15, further comprising a second burr hole anchor configured to secure to the tissue at a second burr hole, wherein the second anchor is configured to receive and immobilize the second therapy catheter as it passes through the second burr hole.

17. The system of claim 15, further comprising an infusion pump fluidly coupled to the supply port of the flow splitter such that fluid contained within the pump is deliverable to the flow apertures of the first and second therapy catheters.

18. The system of claim 15, wherein one or both of the first filter element and the second filter element comprises an elongate cylinder having first and second ends, and wherein one or both of the first filter element and the second filter element is counterbored from each of the first and second ends to form first and second wells, respectively.

19. The system of claim 15, wherein the distal ends of one or both of the first and second therapy catheters comprises a reduced diameter portion.

20. The system of claim 19, wherein one or both of the first and second flow restrictors are positioned within the reduced diameter portion of the first and second therapy catheters, respectively.

21. The system of claim 15, wherein the first and second flow restrictors comprise first and second capillary tubes, respectively.

22. The system of claim 21, wherein the first capillary tube and the second capillary tube are flow-matched capillary tubes.

* * * * *